United States Patent [19]
Thornton

[11] Patent Number: 5,830,181
[45] Date of Patent: Nov. 3, 1998

[54] PERFUSION CATHETER WITH HIGH FLOW DISTAL TIP

[75] Inventor: Troy L. Thornton, San Francisco, Calif.

[73] Assignee: Advanced Cardiovascular Systems, Inc., Santa Clara, Calif.

[21] Appl. No.: 796,880

[22] Filed: Feb. 7, 1997

[51] Int. Cl.[6] .................................................. A61M 29/00
[52] U.S. Cl. ............................................ 604/102; 604/96
[58] Field of Search ..................................... 604/96–102

[56] References Cited

U.S. PATENT DOCUMENTS

| | | | |
|---|---|---|---|
| 4,790,315 | 12/1988 | Mueller, Jr. et al. | 128/344 |
| 5,087,247 | 2/1992 | Horn et al. | 604/98 |
| 5,137,513 | 8/1992 | McInnes et al. | 604/96 |
| 5,195,971 | 3/1993 | Sirhan | 604/96 |
| 5,295,961 | 3/1994 | Niederhauser et al. | 604/96 |
| 5,334,154 | 8/1994 | Samson et al. | 604/102 |
| 5,370,617 | 12/1994 | Sahota | 604/102 |
| 5,542,925 | 8/1996 | Orth | 604/102 |
| 5,571,089 | 11/1996 | Crocker | 604/102 |
| 5,573,508 | 11/1996 | Thorton | 604/96 |
| 5,591,129 | 1/1997 | Shoup et al. | 604/96 |

*Primary Examiner*—Ronald Stright
*Assistant Examiner*—Deborah Blyveis
*Attorney, Agent, or Firm*—Heller, Ehrman, White & McAuliffe

[57] ABSTRACT

A perfusion catheter of the invention has an improved short, distal perfusion portion with a high flow rate. The distal perfusion portion has at least two rows of circumferentially disposed perfusion ports and is preferably tapered in the distal direction from larger cross-sectional dimensions to smaller cross sectional dimensions, with the number of perfusion ports in the most distal row of circumferentially disposed perfusion ports being less than the number of a perfusion ports in a row of perfusion ports proximal to the most distal row. The distal perfusion portion is most conveniently formed from a distal skirt of a dilatation balloon on the distal section of the catheter.

9 Claims, 4 Drawing Sheets

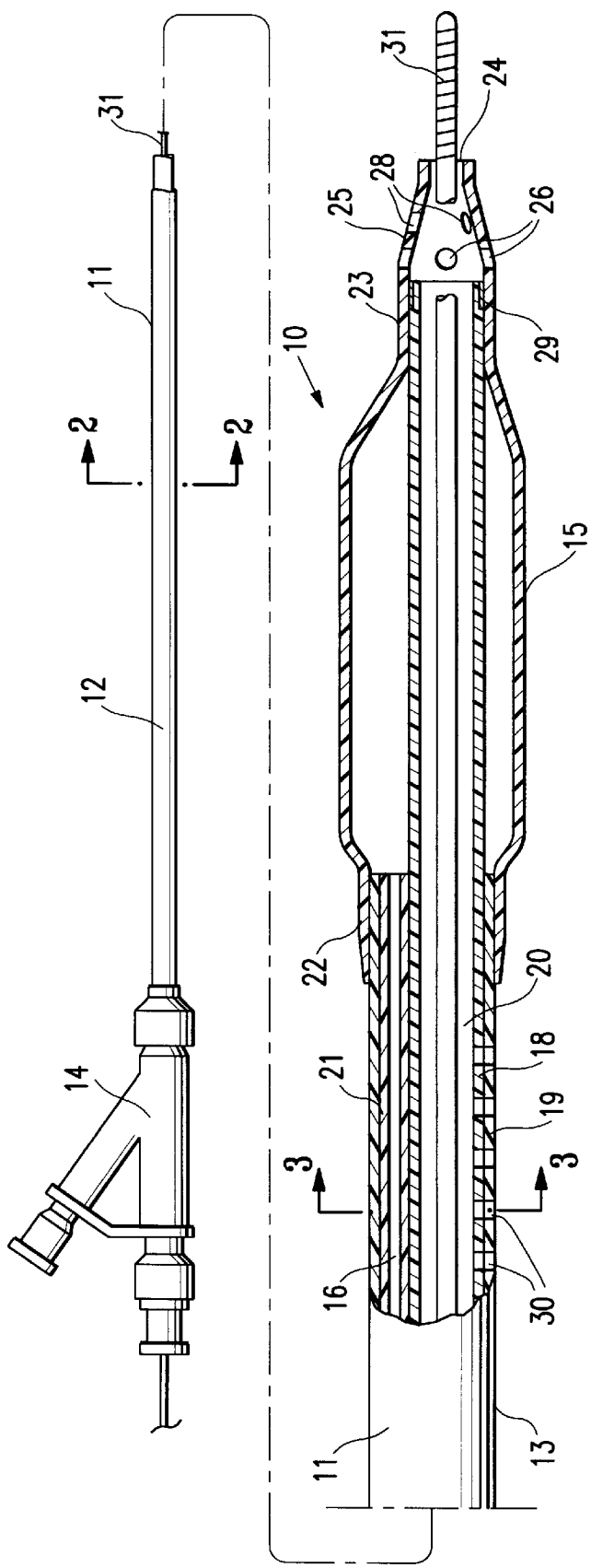
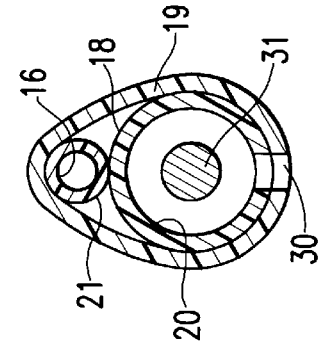
FIG. 1
FIG. 2
FIG. 3

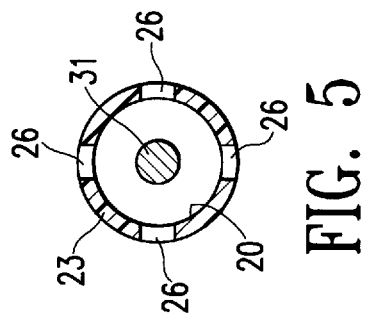
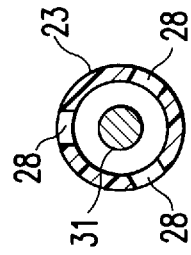
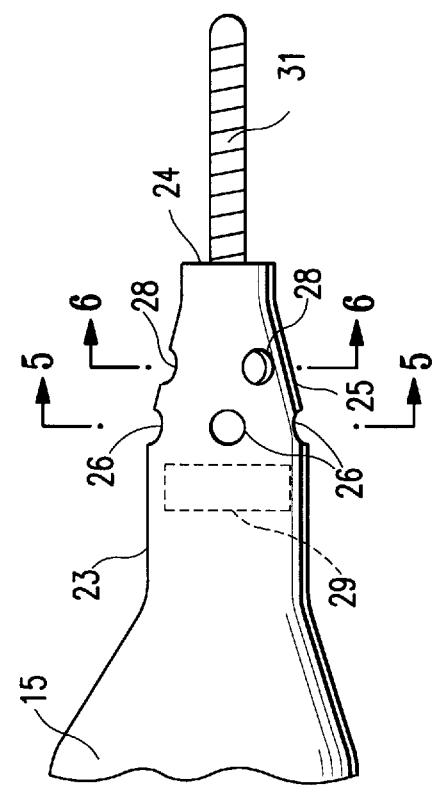

PERFUSION CATHETER WITH HIGH FLOW DISTAL TIP

BACKGROUND OF THE INVENTION

This invention generally relates to perfusion type intravascular catheters, particularly catheters for use in percutaneous transluminal coronary angioplasty (PCTA).

In a typical PTCA procedure a dilatation balloon catheter is advanced over a guidewire to a desired location within the patient's coronary anatomy where the balloon of the dilatation catheter is properly positioned within the stenosis to be dilated. The balloon is then inflated to a predetermined size with radiopaque liquid at relatively high pressures ( generally 4–12 atmospheres) to dilate the stenosed region of the diseased artery. One or more inflations may be needed to effectively dilate the stenosis. The catheter may then be withdrawn from the stenosis or advanced further into the patient's coronary anatomy to dilate additional stenoses.

A high number of angioplasty procedures result in a dissected arterial lining which can collapse causing an acute closure of the arterial passageway. When an acute closure of the arterial passageway occurs, a perfusion device is usually advanced over the in-place guidewire to ensure adequate blood flow distal to the dissected lining until the lining be resecured to the artery wall or a by-pass procedure commenced. Preferably, a dilatation balloon catheter with perfusion capabilities is advanced over the in-place guidewire until the balloon crosses the dissection and then the balloon is inflated to press the dissected lining into place against the arterial wall. With the balloon inflated, blood is caused to pass through a perfusion passageway through the balloon to discharge the blood distal to the catheter. In this manner, the balloon remain in an inflated condition for sufficiently long periods of time, e.g. from about 0.5 to about 6 hours, for the natural healing process to resecure the dissected lining to the arterial wall. Balloon dilatation catheters with perfusion capabilities have been available from Advanced Cardiovascular Systems, Inc. for a number of years, including the RX Perfusion Corona Dilatation Catheter, which has met with much commercial success. Such catheters are described in U.S. Pat. No. 5,496,275 (Sirhan et al) an U.S. application Ser. No. 08/183,574, filed on Jan. 18, 1994 which are incorporated herein by reference in their entirety. The perfusion catheters presently on the market are predominantly rapid exchange type dilatation catheters due to the frequent need to advance a perfusion catheter over an in-place guidewire when an acute occlusion occurs aft the original dilatation catheter has been deflated and withdrawn from the stenotic region.

SUMMARY OF THE INVENTION

This invention is directed to a perfusion type intravascular catheter which has a short, flexible distal shaft section which provides high perfusion flow rates.

The perfusion catheter of the invention generally has an elongated shaft with a proximal end, a distal end, a guidewire lumen extending through at least the distal portion of the catheter and a port in the distal end in fluid communication with the guidewire lumen. The elongated catheter has a first plurality of perfusion ports in the distal portion of the catheter located proximal to the distal end of the catheter and in fluid communication with the guidewire lumen and a second plurality of perfusion ports in a distal portion of the catheter located proximal to the first plurality of perfusion ports.

The length of the distal portion having the first plurality of perfusion ports is relatively short and generally is less than three mm, preferably less than 2 mm. The first plurality of perfusion ports in the distal portion of the catheter are aligned circumferentially in at least two rows, and preferably are about 0.01 to about 0.02 mm in maximum dimension. The rows of circumferentially disposed perfusion ports are longitudinally spaced from each other about 0.2 to about 0.4 mm, preferably about 0.25 to about 0.35 mm. The length of the distal portion of the catheter having the first plurality of perfusion ports is preferably tapered distally from larger to smaller outer dimensions. A first circumferentially disposed row of perfusion ports should preferably have at least about 4 ports and a second circumferentially disposed row distal to the first row should preferably have at least about 3 ports. The ports in adjacent rows can be longitudinally aligned with each other or staggered.

One presently preferred embodiment is directed to a dilatation catheter having an inflatable balloon on a distal portion of the catheter shaft. The distal skirt of the inflatable balloon extends beyond the distal end of an inner tubular member, which extends through the interior of the balloon and defines the guidewire lumen therein, and defines the guidewire lumen beyond the distal end of the inner tubular member. The distal balloon skirt extending beyond the distal end of the inner tubular member includes the length of the distal portion of the catheter having the first plurality of perfusion ports.

The relatively short flexible distal tip having the first plurality of perfusion ports facilitates a high flow rate of oxygenated blood through the guidewire lumen and out the distal end of the distal portion of the catheter. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is an enlarged elevational view of the distal portion of the catheter shown in FIG. 1.

FIG. 5 is a transverse cross-sectional view of the catheter shown in FIG. 4 taken along the lines 5—5.

FIG. 6 is a transverse cross-sectional view of the catheter shown in FIG. 4 taken along the lines 6—6.

DETAILED DESCRIPTION OF THE INVENTION

Figure 7:
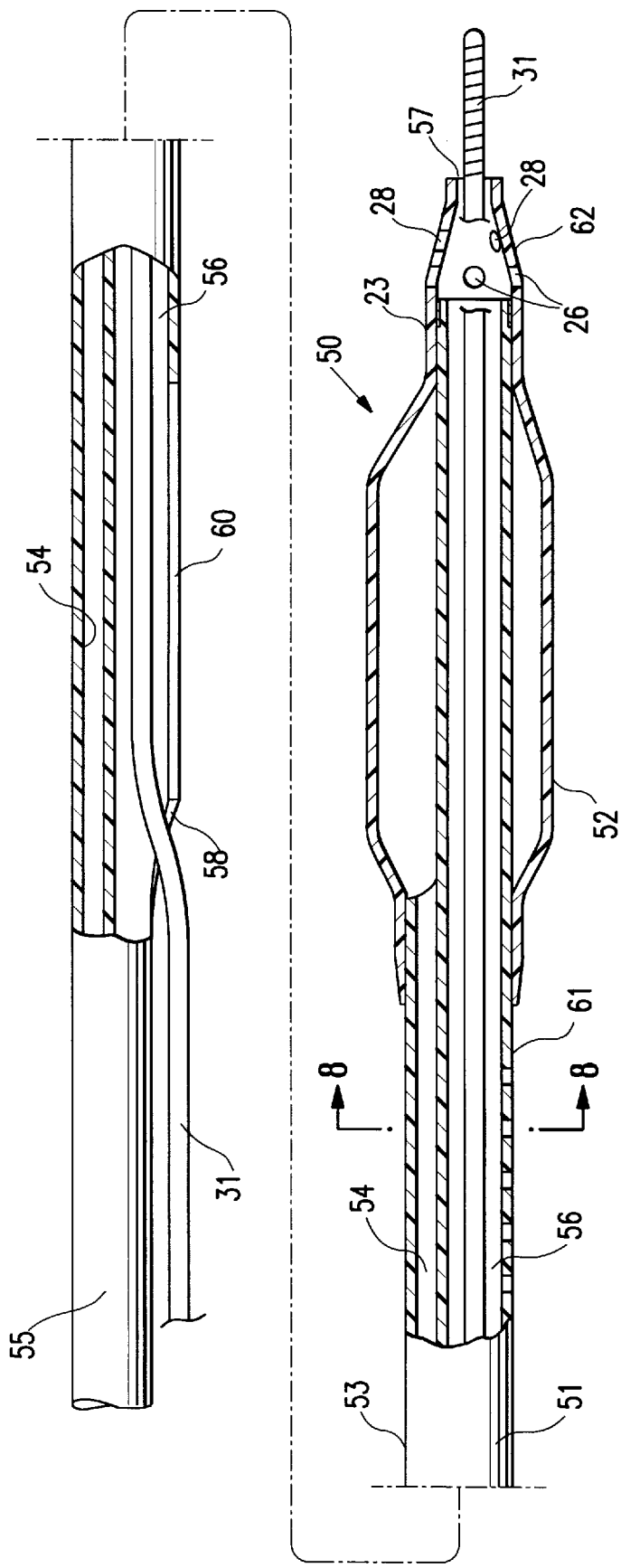
FIG. 7 is an elevational view of the distal portion of another alternative embodiment of the invention wherein the catheter is of a rapid exchange type dilatation catheter.

Reference is made to FIGS. 1–6 which schematically illustrate perfusion dilatation catheter 10 embodying features of the invention. Catheter 10 has an elongated shaft 11 with proximal and distal shaft sections 12 and 13, an adapter 14 on the proximal end of the shaft and a dilatation balloon 15 on the distal shaft section spaced proximal to the distal end. An inflation lumen 16 extends between the proximal end of shaft 11 and a location spaced proximal to the distal end 16 and is in fluid communication with the interior of the dilatation balloon 15. The catheter shaft 11 is provided with a first inner tubular member 18 and an outer tubular member or jacket 19 of suitable polymeric material. A guidewire receiving lumen 20 extends within both the proximal and distal shaft sections 12 and 13. In the distal shaft section 12, the lumen 20 is defined at least in part by the first inner tubular member 18. The distal shaft section 13 is also provided with a second inner tubular member 21 which defines the inflation lumen 16 therein. The outer tubular member 19 secures the inner tubular members 18 and 21 and preferably is bonded to the exterior surface of first tubular member 17 by suitable means such as a suitable adhesive or heat or fusion bonding. Additionally, the outer tubular member 19 may be heat shrunk onto the inner tubular members 18 and 21.

The balloon 15 has a proximal skirt 22 which is secured to distal end of the outer tubular member 19 and a distal skirt 23 which is secured to the distal end of the first inner tubular member 18 and which extends beyond the distal end of the inner tubular member forming the guidewire lumen 20 from the distal end of the first inner tubular member the distal port 24 in the distal end of the catheter. A distal perfusion portion 25 of the distal shaft section 13 is formed at least in part by the portion of the distal skirt 23 which extends beyond the distal end of the first inner tubular member 18 and it is preferably tapered as shown. Four perfusion ports 26 are disposed circumferentially about the axis 27 of the catheter shaft 11 at the large diameter end of the distal perfusion section and three perfusion ports 28 are disposed circumferentially about the axis 27 of the catheter shaft at the small diameter end of the distal perfusion section. A radiopaque marker 29 is provided at the distal end of the first inner tubular member 18 to facilitate fluoroscopic observation thereof within the patient's vasculature, particularly the patient's coronary anatomy. A proximal perfusion portion 30 of the distal shaft section 13 is located proximal to the balloon 15. Typically, the proximal perfusion portion 30 has about 8 to about 12 perfusion ports 31 which extend through the secured or bonded walls of the first inner tubular member 18 and the outer tubular member 19. While a plurality of ports 31 are depicted in the drawing, a single elongated perfusion port can be employed in the proximal perfusion portion 30 in lieu of a plurality of ports 31.

The outer tubular member or jacket 19 may be formed of suitable polymeric material such as polyethylene, a polyester such as Hytrel® (trademark of Dupont), polyetheretherketone (PEEK) or a variety other polymeric materials. See, for example, the discussions of high modulus polymeric materials for catheter shafts found in U.S. application Ser. No. 08/280,210, filed on Jul. 25, 1994, which is incorporated herein by reference in its entirety. The first inner tubular member 18 may be formed of the same material as the outer tubular member 19 or a lubricous material such a fluoropolymer or a hydrophilic material, e.g. the ethylene ethyl acrylate copolymer described in copending application Ser. No. 08/279,239, filed on Jul. 22, 1994, which is incorporated herein by reference in entirety. The low friction surface of the guidewire receiving lumen 20 facilitates the advancement of a guidewire 31 within the guidewire receiving lumen defined by the first inner tubular member 18. The first inner tubular member 18 typically has an outer diameter of about 0.036 inch (0.9 mm) an inner diameter of about 0.033 inch (0.8 mm). The second inner tubular member 21 typically has an outer diameter of about 0.044 inch (1.1 mm) and an inner diameter of about 0.040 inch (1 mm).

Figure 8:
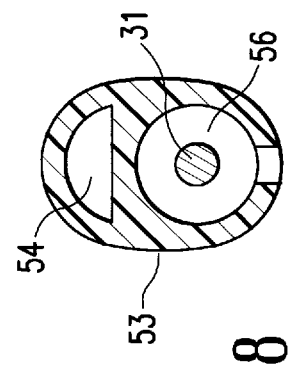
FIG. 8 is a transverse cross-sectional view of the catheter shown in FIG. 7, taken along the lines 8—8.
Figure 10:
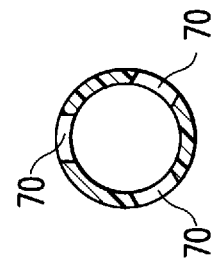
FIG. 10 is a transverse cross-sectional view of the catheter shown in FIG. 9 taken along the lines 10—10.

FIGS. 7 and 8 schematically illustrate another embodiment of the invention wherein the perfusion dilatation catheter 50 is provided with rapid exchange characteristics such as described in U.S. Pat. No. 5,040, (Yock), U.S. Pat. No. 4,748,982 Horzewski et al), U.S. Pat. No. 5,496,275 (Sirhan et al) and U.S. application Ser. No. 08/183,574, filed on Jan. 18, 1994 which have been incorporated herein. The catheter 50 generally has an elongated catheter shaft 51 and an inflatable dilatation balloon 52 on the distal shaft section 53. An inflation lumen 54 extends within the proximal shaft section 55 and the distal shaft section 53 to a location spaced proximal to the distal end of the catheter shaft 51 and is in fluid communication with the interior of the balloon 52. A guidewire receiving lumen 56 extends from the distal port 57 in the distal end of the catheter shaft 51 to a proximal port 58 spaced proximal to the distal end of the catheter shaft.

The distal shaft section 53, as best shown in FIG. 8, has a dual lumen construction and generally is formed by extruding into that form. Alternatively, the distal shaft section may have a first inner tubular member, a second inner tubular member which defines the inflation lumen 54 within the distal shaft section and an outer tubular member or jacket which surrounds and secures together the first and second tubular members as in the prior embodiment. A slit 60 is preferably provided through the wall defining the guidewire lumen 56 which extends from the proximal port 58 to a location spaced proximal to the proximal perfusion portion 61 of the distal shaft section 53. The distal perfusion portion 62 is shown as being essentially the same as in FIGS. 1–6 and is similarly numbered.

Figure 9:
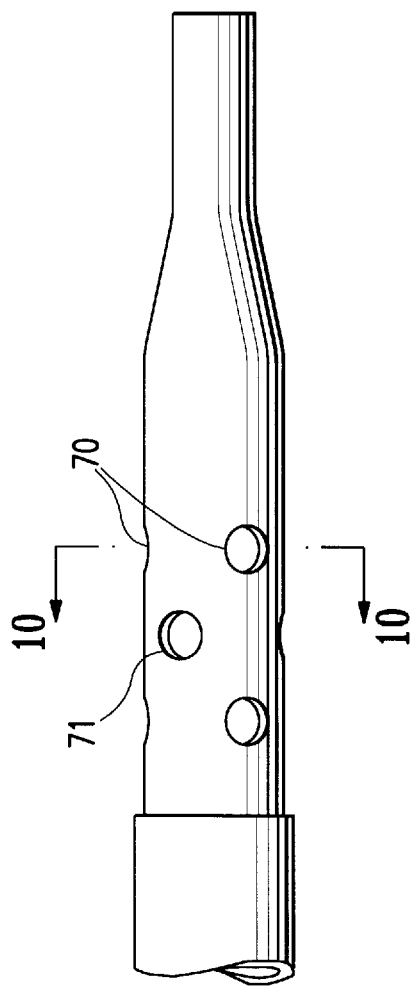
FIG. 9 is an elevational view of an alternative embodiment in which the perfusion ports in adjacent rows of perfusion ports are staggered.

FIG. 9 illustrates a distal tip of a perfusion catheter wherein the ports 70 in a first row of circumferentially arranged perfusion ports are staggered with respect to the perfusion ports 71 in a second row of circumferentially arranged perfusion ports located adjacent to the first row.

To the extent not described herein or in any of the U.S. patents or patent applications which have been incorporated herein by reference, the dimensions, structural details and materials of construction may follow conventional practice for intravascular catheters such as balloon dilatation catheters used in angioplasty procedures.

Various changes and modification may be made to the present invention without departing from the scope of the invention. Moreover, although individual features of the several embodiments of the invention may be shown in some of the drawings and not in others, those skilled in the art will recognize that individual features of one embodiment of the invention can be combined with any or all the features of another embodiment. For example, the construction of the distal shaft section of the catheter shown in FIGS. 1–6 could be that shown in FIGS. 7 and 8, i.e. the distal shaft section could be of a extruded dual lumen.

What is claimed is:

1. A perfusion dilatation catheter, comprising:
   a) an elongated shaft having a proximal end, a distal end, a guidewire lumen, an inflation lumen, a port in the distal end in fluid communication with the guidewire lumen;
   b) a balloon on a distal section of the elongated shaft having an interior in fluid communication with the inflation lumen;
   c) a proximal shaft portion which has at least one perfusion port located proximal to the balloon; and d) a distal shaft portion located distal to the balloon, having a plurality of perfusion ports disposed circumferentially in at least two rows over an axial length less than about 3 mm in fluid communication with the guidewire lumen extending therein.

2. The dilatation catheter of claim 1 wherein the distal shaft portion has a plurality of perfusion ports over a length less than about 2 mm.

3. The dilatation catheter of claim 1 wherein the perfusion ports in the distal shaft portion are about 0.01 to about 0.02 mm in maximum dimension.

4. The dilatation catheter of claim 1 wherein the rows of circumferentially disposed perfusion ports are longitudinally spaced from each other a distance of about 0.2 to about 0.4 mm.

5. The dilatation catheter of claim 4 wherein a first row of perfusion ports has at least three perfusion ports.

6. The dilatation catheter of claim 5 wherein a second row of perfusion ports has at least four perfusion ports and is located distal to the first row of perfusion ports.

7. The dilatation catheter of claim 1 wherein said length extends to the distal end of the shaft and is tapered distally from larger outer dimensions to smaller outer dimensions over substantially the entire length.

8. An intravascular perfusion catheter, comprising:
a) an elongated shaft having a proximal end, a distal end, a guidewire lumen, a port in the distal end in fluid communication with the guidewire lumen, and
   i) a distal perfusion portion of the elongated shaft which extends to a distal extremity of the catheter, having a length less than 3 mm, and having a plurality of perfusion ports disposed circumferentially in at least two rows in fluid communication with the guidewire lumen over the length less than 3 mm, and
   ii) a proximal perfusion portion of the elongated shaft which has at least one perfusion port in fluid communication with the guidewire lumen and which is located proximal to the distal perfusion portion.

9. The catheter of claim 8 wherein the distal perfusion portion of the elongated shaft is tapered over substantially the entire length.

* * * * *